(12) United States Patent
Patel et al.

(10) Patent No.: US 12,251,361 B2
(45) Date of Patent: *Mar. 18, 2025

(54) SOLUTIONS FOR ORAL DOSAGE

(71) Applicant: LIQMEDS WORLDWIDE LIMITED, Middlesex (GB)

(72) Inventors: Vijay Patel, Ahmedabad (IN); Sandip Pareshbhai Mehta, Ahmedabad (IN); Manish Umrethia, Ahmedabad (IN); Jayanta Kumar Mandal, Ahmedabad (IN)

(73) Assignee: LIQMEDS WORLDWIDE LIMITED, Hayes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,575

(22) Filed: May 2, 2023

(65) Prior Publication Data

US 2023/0263747 A1    Aug. 24, 2023

Related U.S. Application Data

(63) Continuation of application No. 17/641,330, filed as application No. PCT/IB2020/052355 on Mar. 16, 2020.

(30) Foreign Application Priority Data

Mar. 15, 2019  (IN) ............... 201921010262

(51) Int. Cl.
| | | |
|---|---|---|
| A61K 31/135 | (2006.01) | |
| A61K 9/00 | (2006.01) | |
| A61K 9/08 | (2006.01) | |
| A61K 47/10 | (2017.01) | |
| A61K 47/26 | (2006.01) | |

(52) U.S. Cl.
CPC .......... *A61K 31/135* (2013.01); *A61K 9/0053* (2013.01); *A61K 9/08* (2013.01); *A61K 47/10* (2013.01); *A61K 47/26* (2013.01)

(58) Field of Classification Search
CPC combination set(s) only.
See application file for complete search history.

(56) References Cited

U.S. PATENT DOCUMENTS

| | | | |
|---|---|---|---|
| 3,428,735 A | 2/1969 | Engelhardt | |
| 6,267,985 B1 | 7/2001 | Chen et al. | |
| 2002/0028789 A1 | 3/2002 | Ford | |
| 2002/0029798 A1* | 3/2002 | Miyoshi | H01L 31/202 136/244 |
| 2003/0004134 A1 | 1/2003 | Serdyuk | |
| 2003/0082214 A1 | 5/2003 | Williams et al. | |
| 2008/0014252 A1 | 1/2008 | DelPrete | |
| 2009/0023705 A1 | 1/2009 | Roberts et al. | |
| 2010/0099639 A1 | 4/2010 | Terao et al. | |
| 2013/0035362 A1 | 2/2013 | Demopulos et al. | |
| 2020/0197326 A1 | 6/2020 | Greco | |

FOREIGN PATENT DOCUMENTS

| | | |
|---|---|---|
| CN | 108272776 A | 7/2018 |
| DE | 102017215154 A1 | 2/2019 |
| FR | 3065371 A1 | 10/2018 |

OTHER PUBLICATIONS

Public Drug Database of France (LAROXYL 40 mg/ml, oral solution—Patient information leaflet; Patient Information Leaflet—LAROXYL 40 mg/ml oral solution—Public Medicines Database (medicaments.gouv.fr); web.archive.org/web/20171001122852/https://base-donnees-publique.medicaments.gouv.fr . . . (Year: 2018).*
Wockhardt; reviewed in 2018, according to the wayback machine capture on Oct. 20, 2021; https://web.archive.org/web/20211020105814/https://www.medicines.org.uk/emc/files/pil.2350.pdf (Year: 2018).*
Public Drug Database of France (LAROXYL 40 mg/ml, oral solution—Patient information leaflet; Patient Information Leaflet—LAROXYL 40 mg/ml oral solution—Public Medicines Database (medicaments.gouv.fr) (Year: 2017).*
Garwood; "Osmotic Diuretics" in Critical Care Nephrology (Second Edition), 2009), as cited https://www.sciencedirect.com/topics/medicine-and-dentistry/glycerol#:~:text=Glycerin%20may%20be%20given%20both,associated%20with%20this%20adverse%20event (Year: 2009).*
Wockhardt; https://web.archive.org/web/20211020105814/https://www.medicines.org.uk/emc/files/pil.2350.pdf (Year: 2018).*
Bonnefont-Rousselot et al. "Antioxidant Effect of Ethanol toward In Vitro Peroxidation of Human Low-Density Lipoproteins Initiated by Oxygen Free Radicals"; 2001; Radiation Research; 155: 279-287; https://doi.org/10.1667/0033-7587(2001)155[0279:AEOETI]2.0.CO;2 (Year: 2001).*
PCT International Search Report for PCT Application No. PCT/IB2020/052355 mailed Aug. 7, 2020 (6 pages).
PCT Written Opinion for PCT Application No. PCT/IB2020/052355 mailed Aug. 7, 2020 (9 pages).
PCT International Preliminary Report on Patentability for PCT Application No. PCT/IB2020/052355 mailed Sep. 16, 2021 (10 pages).
Allen, LV, Jr., "Amitriptyline Hydrochloride 1-mg/ml Oral Liquid and Gel," Int. J. Pharm. Compound., 1999, 3(3):218.
Enever et al., "Factors Influencing Decomposition Rate of Amitriptyline Hydrochlodide in Aqueous Solution," JJ. Pharm. Sci., 1977, 66(8):1087-1089.

(Continued)

*Primary Examiner* — Timothy P Thomas
(74) *Attorney, Agent, or Firm* — Merchant & Gould P.C.; Daniel R. Evans

(57) ABSTRACT

Pharmaceutical compositions comprising a vehicle, a solubilizer, and a surfactant are disclosed to be used in conjunction with non-chemotherapeutic active pharmaceutical ingredients which are soluble in water but subject to hydrolysis to some extent. Such non-chemotherapeutic active pharmaceutical ingredients may include amitriptyline, a derivative thereof, or a combination thereof. The pharmaceutical compositions may be administered as an oral solution. Other embodiments are directed towards methods of using and methods of making such formulations.

7 Claims, No Drawings

(56) References Cited

OTHER PUBLICATIONS

Gupta, "Chemical Stability of Amitriptyline Hydrochloride in Oral Liquid Dosage Forms," Int. J. Pharm. Compounding, 2009, 13(5):445-446.
Strickley, "Solubilizing Excipients in Oral and Injectable Formulations," Pharmaceutical Research, 2004, 21(2):201-230.
Zyryanova et al., "Analgesic Rectal Suppositories Containing a Nonsteroidal Anti-Inflammatory Drug in Combination with Tricyclic Antidepressant and Transmucosal Conductor," Pharmaceutical Chemistry Journal, 2018, 52(9):786-789.
Allen, L.V., Amitriptyline 20 mg/mL in Ora-Plus: Ora-Sweet Suspension, Int. J. Pharm. Compound. (2017) 21(6): 490.
Amitriptyline—Teofarma (20 mL), world.openfoodfacts.org/product/3400930573259/amitriptyline-teofarma, accessed on Apr. 28, 2023.
Amitriptyline Hydrochloride 25mg/5ml Oral Solution—Summary of Product Characteristics (SmPC)—(2022).
Amitriptyline Hydrochloride in Trissel's Stability of Compounded Formulations (Trissel et al., eds.) 6th Ed. (2018) pp. 36-37.
Amitriptyline Hydrochloride monograph from European Pharmacopoeia 5.0 (2005), pp. 980-981.
Amitriptyline, Monograph No. 511 of The Merck Index, 12th Ed. (1996) pp. 511-512.
Elavil® (Amitriptyline Hydrochloride) Tablets, Product Monograph (2010).
European Medicines Agency, List of nationally authorised amitriptyline products, Laroxyl by Teofarma (2015), pp. 1-18.
Nahata, M.C., Long-term stability of zonisamide, amitriptyline, and glycopyrrolate in extemporaneously prepared liquid dosage-forms at two temperatures, Int. J. Pharm. Compound. (2016) 20(2): 164-166.
Ora-Plus® Oral Suspending Vehicle, Product Information (2010).
Ora-Sweet® Flavored Syrup Vehicle, Product Information (2010).
Polonini et al., Stability of Allopurinol, Amitriptyline Hydrochloride, Carbamazepine, Domperidone, Isoniazid, Ketoconazole, Lisinopril, Naproxen, Paracetamol (Acetaminophen), and Sertraline Hydrochloride in SyrSpend SF PH4 Oral Suspensions, Int. J. Pharm. Compound. (2016) 20(5): 426-434.
Solutions and Phase Equilibria (in part), Chapter 16 of Remington's Pharmaceutical Sciences, (Osol et al., eds.) 16th Ed. (1980), pp. 202-203.
SyrSpend® SF PH4 Product information, available at uk.fagron.com/en-GB/product/syrspendr-sf-ph4-liquid, accessed on Apr. 28, 2023.
Susan Garwood, Chapter 104—Osmotic Diuretics in Critical Care Nephrology (Second Edition), Ronco et al. Eds.; W. B. Saunders, 2009, pp. 552-555 (ISBN 9781416042525).
National Park Service's Conserve O Gram, Oct. 11, 2018 Wayback capture: https://web.archive.org/web/20181011092053/www.nps.gov/museum/publications/conserveogram/11-05.pdf (4 pp.).
Jul. 28, 2018 Wayback capture of MedlinePlus entry for osmotic diuresis, https://web.archive.org/web/20180728032242/https://medlineplus.gov/ency/article/001266.htm (2 pp.).
Direct Rx's 2015 Amitriptyline Hydrochloride film-coated tablet product information available on dailymed.nlm.nih.gov/dailymed/fda/fdaDrugXsl.cfm?setid=84600bfc-bcbf-4b37-a575-a6a99e2434fd&type-display, last accessed on Aug. 20, 2024 (14 pp.).
AA Pharma Inc's 2010 Elavil® Amitriptyline Hydrochloride Tablets product information (17 pp.).
Sandoz's 2014 Amitriptyline Hydrochloride Tablets production information for ANDA085968 (4 pp.).
Monograph 511 related to amitriptyline hydrochloride, Merck Index (1996), 3 pp.
Remington's Pharmaceutical Sciences (1980), 4 pp.
Handbook of Pharmaceutical Excipients, pp. 17-19, 283-286, 385-387, 549-553, and 619-620, 2006 (19 pp.).

\* cited by examiner

SOLUTIONS FOR ORAL DOSAGE

RELATED APPLICATIONS

This application is a continuation of U.S. patent application Ser. No. 17/641,330, which is a National Stage Application of PCT/IB2020/052355, filed Mar. 16, 2020, which claims priority to Indian Patent Application number 201921010262 filed on Mar. 15, 2019.

FIELD OF THE INVENTION

The present invention relates a pharmaceutical composition comprising a vehicle, a solubilizer, and a surfactant are disclosed to be used in conjunction with non-chemotherapeutic active pharmaceutical ingredients which are soluble in water but subject to hydrolysis to some extent which is amitriptyline. The pharmaceutical compositions may be administered as an oral solution. Other embodiments are directed towards methods of using and methods of making such formulations.

BACKGROUND OF THE INVENTION

Amitriptyline hydrochloride (HCl) is a dibenzocycloheptene-derivative tricyclic antidepressant (TCA) and analgesic. Amitriptyline may be used to treat neuropathic pain or conditions associated therewith.

Amitriptyline HCl, 3-(10,11-dihydro-5H-dibenzo[a,d]cycloheptene-5-ylidene)-N,N-dimethyl-1-propanamine hydrochloride, is a white, odorless, crystalline compound which is freely soluble in water. Its empirical formula is $C_{20}H_{23}N \cdot HCl$ and its structural formula is:

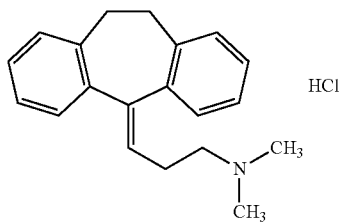 [SMILES: CN(C)CCC=C1c2ccccc2CCc2ccccc21 ; Cl]

Market formulations are in a solid oral dosage form as tablets. Commercially, amitriptyline HCl is supplied as 10 mg, 25 mg, 50 mg, 75 mg, 100 mg or 150 mg tablets. Each tablet contains the following inactive ingredients: colloidal silicon dioxide, hypromellose, lactose monohydrate, magnesium stearate, microcrystalline cellulose, polyethylene glycol, polysorbate, sodium starch glycolate and titanium dioxide. The 10 mg tablets also contain FD&C blue #1 lake. The 25 mg tablets also contain D&C yellow #10 lake and FD&C blue #2 lake. The 50 mg tablets also contain synthetic black iron oxide, synthetic red iron oxide and synthetic yellow iron oxide. The 75 mg tablets also contain FD&C yellow #6 lake. The 100 mg tablets also contain D&C red #33 lake and FD&C red #40 lake. The 150 mg tablets also contain FD&C blue #2 lake and FD&C yellow #6 lake.

Certain individuals may have difficulty swallowing the tablet forms. Further, the tablets must be cut into pieces to yield the lower dosages that children generally require. It is known that "pill splitting" can adversely affect dosage accuracy and the stability of medications. Further, when pill splitting is used, either a crushed tablet or contents of the capsule generally must be mixed with solid food or drink to make them palatable for a child to ingest. Hence, it is desirable to have a liquid formulation of amitriptyline, but such formulations are not available commercially due to many issues with formulating the drug in a liquid form, including problems with stability.

Accordingly, there still exists a need for a liquid formulation of amitriptyline which is stable, easy to manufacture, which requires fewer excipients, and is easy to administer to children as well as geriatric patients with dose accuracy.

SUMMARY OF THE INVENTION

Embodiments herein are directed to a pharmaceutical composition in the form of a liquid solution for active pharmaceutical ingredients that are soluble in water but still liable to hydrolysis. In some embodiments, a ratio of water and appropriate solvent in the pharmaceutical composition is sufficient to produce a stable product while utilizing a minimum amount of solvent. In some embodiments, the solution comprises an active pharmaceutical ingredient which is soluble in water, a vehicle, a surfactant, and a solubilizer. In some embodiments, the active pharmaceutical ingredient is a non-chemotherapeutic active pharmaceutical ingredient. In some embodiments, the active pharmaceutical ingredient may be selected from amitriptyline, a derivative thereof, or a combination thereof. In some embodiments, the pharmaceutical composition does not include a chemotherapeutic active pharmaceutical ingredient. In some embodiments, the pharmaceutical composition does not include a chemotherapeutic active pharmaceutical ingredient which is soluble to water but liable to hydrolysis.

In some embodiments, the vehicle may be water. In some embodiments, the vehicle may be selected from the group consisting of water, dichloromethane, acetonitrile, ethyl acetate, acetone, propylene carbonate, glycerol, coconut fatty acid diethanolamide, medium and/or long chain fatty acids or glycerides, monoglycerides, diglycerides, triglycerides, structured triglycerides, soyabean oil, peanut oil, corn oil, corn oil monoglycerides, corn oil diglycerides, corn oil triglycerides, polyethylene glycol, caprylocaproylmacroglycerides, caproyl 90, 15 propylene glycol, polyoxyethylenesorbitan fatty acid esters, polyoxyethylene castor oil derivatives, castor oil, cottonseed oil, olive oil, safflower oil, peppermint oil, coconut oil, palm seed oil, beeswax, oleic acid, methanol, ethanol, isopropyl alcohol, butanol, acetone, methyl isobutyl ketone, methyl ethyl ketone, or a combination thereof. In some embodiments, the vehicle may be purified water. In some embodiments, the vehicle is water and is added to the formulation at a quantum sufficient.

In some embodiments, the surfactant may be sorbitan esters (Span), especially from saturated or unsaturated fatty acids, polyethoxylated sorbitan esters (Tween), especially from saturated or unsaturated fatty acids, Caprylocaproyl macrogol-8 glycerides (Labrasol), Lauroyl macrogol-32 glycerides (Gelucire 44/14), stearoyl macrogol-32 glycerides (Gelucire 50/13), especially from saturated or unsaturated fatty acids, polyethoxylated and/or hydrogenated castor oils such as PEG-40 hydrogenated castor oil (Cremophor RH 40®), PEG-60 hydrogenated castor oil (Cremophor RH 60®), PEG-35 castor oil or polyoxyl 35 castor oil (Cremophor EL), Macrogol (25) cetostearyl ether (Cremophor A25), polyethoxylated ethers, especially from saturated or unsaturated fatty alcohols, polyethylene glycol such as PEG 200, poloxamer (Lutrol F 127), alpha tocopherol, polyoxyethylene lauryl ether (Brji 30, Brji 35), polyvinyl caprolactam-polyvinylacetate-polyethyleneglycol graft copolymer (e.g. Soluplus®), PEG-35 castor oil, polysorbate 80, or a combination thereof.

In some embodiments, the solubilizer is glycerol. In some embodiments, the solubilizer may be selected from ethanol, propylene glycol, polyhydric alcohols such as concentrated glycerol, glycerol, polyvinyl alcohol, polyethylene glycol, ethylene glycol, or a combination thereof.

In some embodiments, the pharmaceutical composition may further comprise an antioxidant, a sweetener, a flavoring agent, a buffering agent, a sweetness/flavor enhancing agent, a chelating agent, a preservative, or any combination thereof.

Some embodiments are directed to a methods of using the pharmaceutical composition of embodiments herein for the treatment and/or prevention of diseases or disorders. In some embodiments, the disease or disorder comprises a mental illness. In some embodiments, the disease or disorder comprises major depressive disorder, anxiety disorders, attention deficit hyperactivity disorder, bipolar disorder, migraines, nocturnal enuresis, irritable bowel syndrome, neuropathic pain, fibromyalgia, postherpetic neuralgia, insomnia, or a combination thereof, wherein the active pharmaceutical ingredient is amitriptyline.

In some embodiments, a method of treating depression in a subject in need thereof comprises administering to the subject the pharmaceutical composition of embodiments herein, wherein the active pharmaceutical ingredient is amitriptyline. In some embodiments, a method of treating anxiety in a subject in need thereof comprises administering to the subject the pharmaceutical composition of embodiments herein, wherein the active pharmaceutical ingredient is amitriptyline. In some embodiments, a method of treating attention deficit hyperactivity disorder in a subject in need thereof comprises administering to the subject the pharmaceutical composition of embodiments herein, wherein the active pharmaceutical ingredient is amitriptyline. In some embodiments, a method of treating bipolar disorder in a subject in need thereof comprises administering to the subject the pharmaceutical composition of embodiments herein, wherein the active pharmaceutical ingredient is amitriptyline.

In some embodiments, a method of preventing a migraine headache in a subject in need thereof comprises administering to the subject the pharmaceutical composition of embodiments herein, wherein the active pharmaceutical ingredient is amitriptyline. In some embodiments, a method of preventing neuropathic pain in a subject in need thereof comprises administering to the subject the pharmaceutical composition of embodiments herein, wherein the active pharmaceutical ingredient is amitriptyline.

In some embodiments, the solution comprises about 1% w/v to about 30% w/v active pharmaceutical ingredient, about 0.1% w/v to about 40% w/v solubilizer, about 0.001% w/v to about 20% w/v surfactant, and about 0.1% w/v to about 99% w/v vehicle.

DETAILED DESCRIPTION OF THE INVENTION

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "surfactant" is a reference to one or more surfactants and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with an active pharmaceutical ingredient, can include, but is not limited to, providing the active pharmaceutical ingredient into or onto the target tissue; providing the active pharmaceutical ingredient systemically to a patient by, e.g., intravenous injection whereby the therapeutic reaches the target tissue; providing the active pharmaceutical ingredient in the form of the encoding sequence thereof to the target tissue (e.g., by so-called gene-therapy techniques). "Administering" a composition may be accomplished by injection, topical administration, orally, or by either method in combination with other known techniques. In some embodiments, administering is through an oral route of administration.

The term "subject" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The term "improve" is used to convey that the compounds of embodiments herein change either the appearance, form, characteristics and/or the physical attributes of the tissue to which it is being provided, applied or administered. In some embodiments, the pharmaceutical compositions of embodiments herein comprising amitriptyline are suited to improve symptoms of major depressive disorder.

The term "inhibit" includes the administration of a compound of embodiments herein to prevent the onset of the symptoms, alleviating the symptoms, or eliminating the disease, condition or disorder. In some embodiments, the pharmaceutical compositions of embodiments herein comprising amitriptyline are used to inhibit symptoms of anxiety disorders.

By "pharmaceutically acceptable", it is meant the carrier, diluent or excipient must be compatible with the other ingredients of the formulation and not deleterious to the recipient thereof.

As used herein, the term "therapeutic" means an agent utilized to treat, combat, inhibit, ameliorate, prevent or improve an unwanted condition or disease of a patient. In part, the pharmaceutical compositions of embodiments herein are directed to the treatment of major depressive disorder.

A "therapeutically effective amount" or "effective amount" of a composition is a predetermined amount calculated to achieve the desired effect. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, concomitant therapies and the condition being treated. However, it will be understood that the effective amount administered will be determined by the physician in the light of the relevant circumstances including the condition to be treated, the choice of compound to be administered, and the chosen route of administration, and therefore the above dosage ranges are not intended to limit the scope of embodiments herein in any way. A therapeutically effective amount of a compound of this disclosure is typically an amount such that when it is administered in a physiologically tolerable excipient composition, it is sufficient to achieve an effective systemic concentration or local concentration in the tissue.

The terms "treat," "treated," or "treating," as used herein, refers to both therapeutic treatment and prophylactic or preventative measures, wherein the object is to inhibit, prevent or slow down (lessen) an undesired physiological condition, disorder or disease, or to improve, inhibit, or otherwise obtain beneficial or desired clinical results. For the purposes of this invention, beneficial or desired clinical results include, but are not limited to, improvement or alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein, the term "a derivative thereof" refers to a salt thereof, a pharmaceutically acceptable salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof. In some embodiments, the active pharmaceutical ingredient may be administered as a derivative thereof. In some embodiments, reference to a derivative, e.g. a salt thereof, shall be interchangeable with the active pharmaceutical ingredient or any other derivative thereof. For example, unless otherwise stated, amitriptyline and amitriptyline hydrochloride may be used interchangeably herein.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active pharmaceutical ingredient(s) in the formulation or method that treats the specified condition (e.g. seizures) is the specifically recited therapeutic(s) in the particular embodiment or claim.

Embodiments herein are directed to a pharmaceutical composition in the form of a liquid solution for active pharmaceutical ingredients that are soluble in water but still liable to hydrolysis. An active pharmaceutical agent having a solubility of more than 10 mg/ml in water is both soluble in water and liable to hydrolysis. In some embodiments, a ratio of vehicle and appropriate solubilizer in the pharmaceutical composition is sufficient to produce a stable product while utilizing a minimum amount of solubilizer. The ration of vehicle and solubilizer may be about 1:99%, 10:90%, about 20:80%, about 30:70%, about 40:60%, about 50:50%, about 60:40%, about 70:30%, about 80:20%, about 90:10%, about 99:1%.

In some embodiments, the solution comprises an active pharmaceutical ingredient which is soluble in water, a vehicle, a surfactant, and a solubilizer. In some embodiments, the active pharmaceutical ingredient is a non-chemotherapeutic active pharmaceutical ingredient. In some embodiments, the pharmaceutical composition does not include a chemotherapeutic active pharmaceutical ingredient. In some embodiments, the pharmaceutical composition does not include a chemotherapeutic active pharmaceutical ingredient which is soluble in water but liable to hydrolysis. In some embodiments, the active pharmaceutical ingredient may be selected from amitriptyline, a derivative thereof, or a combination thereof.

In some embodiments, the active pharmaceutical ingredient is in an amount of about 0.1 mg/mL, about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 7 mg/mL, about 8 mg/mL, about 9 mg/mL, about 10 mg/mL, about 12 mg/mL, about 14 mg/mL, about 16 mg/mL, about 18 mg/mL, about 20 mg/mL, about 22 mg/mL, about 25 mg/mL, about 27 mg/mL, about 30 mg/mL, about 40 mg/mL, about 50 mg/mL, about 60 mg/mL, about 70 mg/mL, about 80 mg/mL, about 90 mg/mL, about 100 mg/mL, about 150 mg/mL, about 200 mg/mL, about 250 mg/mL, about 300 mg/mL, about 350 mg/mL, or a range of any two of these values.

In some embodiments, the active pharmaceutical ingredient is in an amount of about 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, about 1% w/v, about 3% w/v, about 5% w/v, about 10% w/v, about 15% w/v, about 20% w/v, about 25% w/v, about 30% w/v, about 35% w/v, about 40% w/v, about 45% w/v, about 50% w/v, about 55% w/v, or a range of any two of these values. In some embodiments, the active pharmaceutical ingredient is in an amount of about 0.01% w/v to about 50% w/v. In some embodiments, the active pharmaceutical ingredient is in an amount of about 0.01% w/v to about 20% w/v. In some embodiments, the active pharmaceutical ingredient is in an amount of about 0.01% w/v to about 10% w/v. In some embodiments, the active pharmaceutical ingredient is in an amount of about 4% w/v.

Vehicles of embodiments herein are the liquid bases which carry drug and other excipients in dissolved or dispersed state and may be selected from aqueous vehicles or non-aqueous vehicles. Examples of suitable vehicles may include, but not limited to, water, propylene glycol, dichloromethane, acetonitrile, ethyl acetate, acetone, propylene carbonate, glycerol, coconut fatty acid diethanolamide, medium and/or long chain fatty acids or glycerides, monoglycerides, diglycerides, triglycerides, structured triglycerides, soyabean oil, peanut oil, corn oil, corn oil monoglycerides, corn oil diglycerides, corn oil triglycerides, polyethylene glycol, caprylocaproylmacroglycerides, caproyl 90, 15 propylene glycol, polyoxyethylenesorbitan fatty acid esters, polyoxyethylene castor oil derivatives, castor oil, cottonseed oil, olive oil, safflower oil, peppermint oil, coconut oil, palm seed oil, beeswax, oleic acid, methanol, ethanol, isopropyl alcohol, butanol, acetone, methyl isobutyl ketone, methyl ethyl ketone, or a combination thereof. In some embodiments, the vehicle may be purified water. In some embodiments, the vehicle is water and is added to the formulation at a quantum sufficit.

The vehicle may be in an amount of about 0.1% w/v, about 1% w/v, about 3% w/v, about 5% w/v, about 10% w/v, about 15% w/v, about 20% w/v, about 25% w/v, about 30% w/v, about 35% w/v, about 40% w/v, about 45% w/v, about 50% w/v, about 55% w/v, about 60% w/v, about 6% w/v, about 70% w/v, about 75% w/v, about 80% w/v, about 85% w/v, about 90% w/v, about 95% w/v, about 99% w/v, or a range of any two of these values. In some embodiments, the vehicle may be in an amount of about 0.1% w/v to about 99% w/v.

Surfactant is a general name for materials that possess surface activity; in solution they tend to orient at the surface of the liquid. There are several general classes of surfactants: anionic, cationic, amphoteric and non-ionic. Surfactants are amphiphilic molecules, i.e. part of the molecule is hydrophilic, and part is lipophilic. This combination of the two opposite affinities in the same molecule causes them to orient to the interface and thereby reduce the interfacial tension between the continuous and disperse phases, such as in emulsions and suspensions. Ionic surfactants work primarily through electrostatic forces, whereas non-ionic surfactants work primarily through steric forces.

In some embodiments, the surfactant may be sorbitan esters (Span), especially from saturated or unsaturated fatty acids, polyethoxylated sorbitan esters (Tween), especially from saturated or unsaturated fatty acids, Caprylocaproyl macrogol-8 glycerides (Labrasol), Lauroyl macrogol-32 glycerides (Gelucire 44/14), stearoyl macrogol-32 glycerides (Gelucire 50/13), especially from saturated or unsaturated fatty acids, polyethoxylated and/or hydrogenated castor oils such as PEG-40 hydrogenated castor oil (Cremophor RH 40®), PEG-60 hydrogenated castor oil (Cremophor RH 60®), PEG-35 castor oil or polyoxyl 35 castor oil (Cremophor EL), Macrogol (25) cetostearyl ether (Cremophor A25), polyethoxylated ethers, especially from saturated or unsaturated fatty alcohols, polyethylene glycol such as PEG 200, poloxamer (Lutrol F 127), alpha tocopherol, polyoxyethylene lauryl ether (Brji 30, Brji 35), polyvinyl caprolactam-polyvinylacetate-polyethyleneglycol graft copolymer (e.g. Soluplus®), PEG-35 castor oil, polysorbate 80, or a combination thereof. In some embodiments, the surfactant may be polysorbate 80.

In some embodiments, the surfactant is in the pharmaceutical composition in an amount of about 0.01 mg/mL, about 0.05 mg/mL, about 0.1 mg/mL, about 0.5 mg/mL, about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 100 mg/mL, about 150 mg/mL, about 200 mg/mL, about 250 mg/mL, about 300 mg/mL, about 350 mg/mL, about 400 mg/mL, about 450 mg/mL, about 500 mg/mL, about 550 mg/mL, about 600 mg/mL, about 650 mg/mL, about 700 mg/mL, about 750 mg/mL, or a range of any two of these values. In some embodiments, the surfactant is in the pharmaceutical composition in an amount of about 0.5 mg/mL to about 660 mg/mL. In some embodiments, the surfactant is in the pharmaceutical composition in an amount of about 1 mg/mL to about 660 mg/mL. In some embodiments, the surfactant is in the pharmaceutical composition in an amount of about 5 mg/mL to about 660 mg/mL. In some embodiments, the surfactant is in the pharmaceutical composition in an amount of about 30 mg/mL.

In some embodiments, the surfactant is in the pharmaceutical composition in an amount of about 0.01% w/v, about 0.1% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v, about 60% w/v, about 65% w/v, about 70% w/v, about 75% w/v, about 80% w/v, about 85% w/v, about 90% w/v, about 95% w/v, about 99% w/v, or a range of any two of these values. In some embodiments, the surfactant is in the pharmaceutical composition in an amount of about 0.01% w/v to about 99% w/v. In some embodiments, the surfactant may be in an amount of about 0.01% w/v to about 50% w/v. In some embodiments, the surfactant may be in an amount of about 0.05% w/v to about 30% w/v. In some embodiments, the surfactant may be in an amount of about 0.05% w/v to about 0.5% w/v. In some embodiments, the surfactant may be in an amount of about 0.1% w/v.

Solubilizers are solvents used in liquid drug formulations to increase the solubility of poorly soluble substances and enhance the chemical stability of a drug. In some embodiments, the solubilizer is glycerol. In some embodiments, the solubilizer may be selected from ethanol, propylene glycol, polyhydric alcohols such as concentrated glycerol, glycerol, polyvinyl alcohol, polyethylene glycol, ethylene glycol, or a combination thereof. Without intending to be limiting, it was surprisingly found that the addition of the solubilizer (e.g. glycerol) exhibits excellent stabilization capability for active pharmaceutical agents which are liable to hydrolysis (e.g. amitriptyline). In some embodiments, the solubilizer is glycerol.

In some embodiments, the solubilizer is in the pharmaceutical composition in an amount of about 0.01 mg/mL, about 0.05 mg/mL, about 0.1 mg/mL, about 0.5 mg/mL, about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 100 mg/mL, about 150 mg/mL, about 200 mg/mL, about 250 mg/mL, about 300 mg/mL, about 350 mg/mL, about 400 mg/mL, about 450 mg/mL, about 500 mg/mL, about 550 mg/mL, about 600 mg/mL, about 650 mg/mL, about 700 mg/mL, about 750 mg/mL, or a range of any two of these values. In some embodiments, the solubilizer is in the pharmaceutical composition in an amount of about 0.5 mg/mL to about 660 mg/mL. In some embodiments, the solubilizer is in the pharmaceutical composition in an amount of about 200 mg/mL to about 660 mg/mL. In some embodiments, the solubilizer is in the pharmaceutical composition in an amount of about 250 mg/mL to about 660 mg/mL. In some embodiments, the solubilizer is in the pharmaceutical composition in an amount of about 380 mg/mL.

In some embodiments, the solubilizer may be in an amount of about 0.1% w/v, about 1% w/v, about 3% w/v, about 5% w/v, about 10% w/v, about 15% w/v, about 20% w/v, about 25% w/v, about 30% w/v, about 35% w/v, about 40% w/v, about 45% w/v, about 50% w/v, about 55% w/v, or a range of any two of these values. In some embodiments, the solubilizer may be in an amount of about 0.1% w/v to about 55% w/v. In some embodiments, the solubilizer may be in an amount of about 38% w/v.

In some embodiments, the liquid pharmaceutical composition is a solution comprising about 1% w/v to about 30% w/v active pharmaceutical ingredient, about 0.1% w/v to about 40% w/v solubilizer, about 0.01% w/v to about 20% w/v surfactant, and about 0.1% w/v to about 99% w/v vehicle.

In some embodiments, the solution comprises about 0.5% w/v to about 30% w/v amitriptyline, about 0.05% w/v to about 20% w/v surfactant, about 0.1% w/v to about 50% w/v solubilizer, and about 0.1% w/v to about 99% w/v vehicle. In some embodiments, the solution comprises about 0.01% w/v to about 5% w/v active pharmaceutical ingredient, about 0.05% w/v to about 0.2% w/v surfactant, about 30% w/v to about 40% w/v solubilizer, and about 0.1% w/v to about 99% w/v vehicle. In some embodiments, the solution comprises about 4% w/v amitriptyline, about 0.1% w/v surfactant, about 38% w/v solubilizer, and about 0.1% w/v to about 99% w/v vehicle. In some embodiments, the solution comprises about 4% w/v amitriptyline, about 38% w/v glycerol, about 0.1% w/v polysorbate 80, and water.

In some embodiments, the pharmaceutical composition may further comprise an antioxidant, a sweetener, a flavoring agent, a buffering agent, a sweetness/flavor enhancing agent, a chelating agent, a preservative, or any combination thereof. In some embodiments, the pharmaceutically acceptable excipient is in an amount of about 0.1% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, or a range of any two of these values.

Preservatives are compounds which are included in pharmaceutical dosage form to prevent the growth of microorganisms during the product's manufacture and shelf life. Examples of the suitable preservatives are, but not limited to, benzyl alcohol, chloro-butanol, chloro-cresol, alkyl esters of parabens, phenol, phenyl ethanol, benzoic acid, potassium sorbate, sodium benzoate and antimicrobial solvents like propylene glycol, chloroform, or a combination thereof.

Antioxidants are substances capable of inhibiting oxidation and that may be added to pharmaceutical products to prevent deterioration by oxidative processes. Examples of suitable antioxidants are but not limited to Butylatedhydroxyanisole (BHA), Butylatedhydroxy toluene (BHT), Sodium metabisulfite, Ascorbic acid, Alphatocopherol, Sodium edetate, or any combination thereof. In some embodiments, the antioxidants are BHA and BHT.

Buffering agents are compounds which provide stability and pH control to the pharmaceutical formulations. Examples of suitable buffering agents are but not limited to sodium acetate, tris(hydroxymethyl)aminomethane (TRIS), triethanolamine, sodium citrate, ammonium sulfate, sodium phosphate, disodium hydrogen phosphate, potassium citrate, citric acid monohydrate, trisodium citrate dehydrate, or a combination thereof.

Chelating agents are compounds which are used for drug stabilization, to maintain potency of active pharmaceutical ingredients and to stabilize colors and flavors. Examples of suitable chelating agents are but not limited to citric acid monohydrate, disodium edetate, dipotassium edetate, edetic acid, fumaric acid, malic acid, phosphoric acid, sodium edetate, tartaric acid, trisodium edetate, or a combination thereof.

Sweetening agents are compounds that impart sweetness and improve patient compliance through taste masking. Examples of the suitable sweetening agents are but not limited to sucralose, sucrose, acesulfame potassium, liquid glucose, glycerin, sorbitol, liquid maltitol, saccharin sodium, aspartame, or a combination thereof. In some embodiments, the sweetening agent is sucralose.

Flavoring agents are the compounds which are added to increase patient acceptance of the drug by masking the specific taste sensations. Examples of suitable flavoring agent are, but not limited to, essential oils including peppermint oil, orange oil or lemon oil, peppermint flavor, fruit flavor (e.g. peach flavor or strawberry flavor), tutti-fruity flavor, mint flavor, or a combination thereof. In some embodiments, the flavoring agent is a peach flavor.

In some embodiments, the solution of embodiments herein is devoid of any viscosity regulating agent.

In some embodiments, the pharmaceutical composition of embodiments herein is a liquid solution. In some embodiments, the liquid solution is suitable for oral administration.

In some embodiments, the pharmaceutical composition of embodiments herein is useful for the manufacture of a medicament. In one of the further embodiments, the pharmaceutical composition of embodiments herein is useful as a medicament.

In some embodiments, the active pharmaceutical ingredient may be administered in combination with one or more additional active pharmaceutical ingredients. In some embodiments, the pharmaceutical composition of embodiments herein may include an additional active pharmaceutical ingredient. In some embodiments, the pharmaceutical composition of embodiments herein may be administered in conjunction with, either concurrently or sequentially, with the additional active pharmaceutical ingredient.

Methods of Treatment

Some embodiments are directed to a methods of using the pharmaceutical composition of embodiments herein for the treatment and/or prevention of diseases or disorders. In some embodiments, the disease or disorder comprises a mental illness. In some embodiments, the disease or disorder comprises major depressive disorder, anxiety disorders, attention deficit hyperactivity disorder, bipolar disorder, migraines, nocturnal enuresis, irritable bowel syndrome, neuropathic pain, fibromyalgia, postherpetic neuralgia, insomnia, or a combination thereof, wherein the active pharmaceutical ingredient is amitriptyline.

In some embodiments, a method of treating depression in a subject in need thereof comprises administering to the subject the pharmaceutical composition of embodiments herein, wherein the active pharmaceutical ingredient is amitriptyline. In some embodiments, a method of treating anxiety in a subject in need thereof comprises administering to the subject the pharmaceutical composition of embodiments herein, wherein the active pharmaceutical ingredient is amitriptyline. In some embodiments, a method of treating attention deficit hyperactivity disorder in a subject in need thereof comprises administering to the subject the pharmaceutical composition of embodiments herein, wherein the active pharmaceutical ingredient is amitriptyline. In some embodiments, a method of treating bipolar disorder in a subject in need thereof comprises administering to the subject the pharmaceutical composition of embodiments herein, wherein the active pharmaceutical ingredient is amitriptyline.

In some embodiments, a method of preventing a migraine headache in a subject in need thereof comprises administering to the subject the pharmaceutical composition of embodiments herein, wherein the active pharmaceutical ingredient is amitriptyline. In some embodiments, a method of preventing neuropathic pain in a subject in need thereof comprises administering to the subject the pharmaceutical composition of embodiments herein, wherein the active pharmaceutical ingredient is amitriptyline.

The liquid pharmaceutical compositions of embodiments herein are proposed to have unexpectedly dramatic dissolution profiles. Rapid dissolution of an administered active pharmaceutical ingredient is preferable, as faster dissolution generally leads to greater bioavailability and faster onset of action. To improve the dissolution profile and bioavailability of an active pharmaceutical ingredient, it would be useful to increase dissolution of the active pharmaceutical ingredient used so that it could attain a level close to 100% dissolution of the drug substance.

The liquid pharmaceutical compositions of embodiments herein comprising the active pharmaceutical ingredient or derivative thereof, exhibit improved or comparable pharmacokinetic profiles as compared to marketed or known compositions of the same active pharmaceutical ingredient or derivative thereof. For example, the Cmax and/or AUC of the liquid pharmaceutical compositions of disclosed herein can be greater than or substantially equal to the Cmax and/or AUC for known or marketed compositions, e.g. solid formulations, administered at the same dose. In addition, the Tmax of the liquid compositions of the present invention can be lower than or substantially equal to that obtained for a known or marketed compositions, administered at the same dose. In addition, combinations of an improved or comparable Cmax, AUC and Tmax profile can be exhibited by the liquid compositions of the invention, as compared to known or marketed compositions. In further aspects, the liquid compositions of the present invention may result in minimal different absorption levels when administered under fed as compared to fasting conditions.

The liquid compositions of embodiments herein exhibit in comparative pharmacokinetic testing with marketed or known formulations, administered at the same dose, a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by the marketed or known formulation.

In some embodiments, the liquid compositions of embodiments herein exhibit in comparative pharmacokinetic testing with marketed or known formulation, administered at the same dose, a Cmax which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the Cmax exhibited by the marketed or known formulation.

In one of the further aspects, the liquid compositions of embodiments herein exhibit in comparative pharmacokinetic testing with marketed or known formulation, administered at the same dose, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least 5 about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the marketed or known formulation.

In some embodiments, the Tmax of the active pharmaceutical ingredient or salt thereof used for the preparation of the liquid composition of embodiments herein, when assayed in the plasma of the mammalian subject, is less than about 6 to about 8 hours. In some embodiments, the Tmax of the active pharmaceutical ingredient or salt thereof is less than about 6 hours, less than about 5 hours, less than about 4 hours, less than about 3 hours, less than about 2 hours, less than about 1 hour, or less than about 30 minutes after administration.

In some aspects, the liquid compositions of embodiments herein exhibit improved or comparable bioavailability as compared to known or marketed compositions.

Methods of Preparing Formulation

A general process for the preparation of the liquid oral pharmaceutical compositions of embodiments above may be as follows:
(a) Mix one or more surfactants and one or more solubilizers under stirring in a vehicle;
(b) Dissolve active pharmaceutical ingredient in the mixture obtained in Step (a);
(c) Add one or more antioxidants, sweeteners, or preservatives in the mixture obtained in Step (b).
(d) Dilute the obtained mixture in Step (c) up to the desired volume with the filler/vehicle;
(e) Add one or more flavoring agents in the final composition obtained in Step (d).

The embodiments illustrating the method and materials used may be further understood by reference to the following non-limiting examples.

EXAMPLES

Example 1: A Liquid Oral Pharmaceutical Composition Comprising Amitriptyline Hydrochloride

| Sr. No. | Ingredients | Role of ingredients | Quantity % w/v | (mg/mL) |
|---|---|---|---|---|
| 1 | Amitriptyline Hydrochloride (equivalent to amitriptyline) | Active | 4 | 40 |
| 2 | Glycerol | Stabilizer/solubilizer | 38 | 380 |
| 3 | Sucralose | Sweetener | 0.5 | 5 |
| 4 | Suitable Flavor | Flavor | 0.02 | 0.2 |
| 5 | Polysorbate 80 | Surfactant | 0.1 | 1 |
| 6 | Purified Water | Vehicle | q.s to 100 ml | Q.S. 1 mL |

Preparation of the formulation above was as follows:
a. Add sufficient quantity of purified water in vessel
b. Add glycerin and mix until homogenously dispersed
c. Add polysorbate 80 and mix until dispersed
d. Add amitriptyline and mix until dissolved
e. Add sucralose and flavor one by one and mix until dissolved
f. Volume make up until it reaches batch size, filter and fill in to suitable packaging Those who are skilled in the art can also understand that some variations in the herein described processes for the preparation of liquid compositions of the present invention can be adopted which are well within the skills of the skilled artisan. One can change sequences of the steps in the above mentioned process for the purposes of suitability and convenience without affecting the quality and characteristics of the resulting product. Some example of variations, without intending it to be limiting, include having a pH in the range of about 3 to about 7, glycerin in an amount of about 200 to about 600 mg/ml, change in the sequence of processing steps, change in the order of addition, adding an alternative surfactant, adding an alternative buffering agent, or the like.

Those who are reasonably skilled in the art can easily understand that similar liquid formulations using other active non-chemotherapeutic agents, including without limitation those mentioned in the above paragraphs with other suitable excipients, also mentioned in the foregoing paragraphs may be prepared in the above mentioned formulas using above mentioned processes for preparation. Such other examples of compositions and processes of preparation thereof are also within the ambit of the invention disclosed and claimed in the present application.

Example 2: Stability Study Results of Amitriptyline Liquid Composition

The oral liquid pharmaceutical composition prepared according to Example 1 exhibits unexpected stability profile when tested after six months:

| Test parameters | Tentative specification | Initial | Storage condition 40° C. ± 2° C./ NMT75% RH 3 M | 6 M | 25° C. ± 2° C./ 60 ± 5% RH 3 M | 6 M |
|---|---|---|---|---|---|---|
| Description | A clear colorless to pale yellow colored solution with characteristic odor. | Complies | Complies | Complies | Complies | Complies |
| pH | Between 3.5 and 5.5 | 4.5 | 4.7 | 4.0 | 4.8 | 4.2 |
| Assay of Amitriptyline | Between 90.0% and 110.0% of labeled amount. | 99.50% | 95.80% | 100.90% | 102.90% | 100.60% |
| Related Substance | | | | | | |
| Impurity -A | Not more than 0.2% | ND | BQL | BQL | BQL | BQL |
| Impurity -B | Not more than 0.2% | 0.08% | 0.08% | 0.07% | 0.08% | 0.08% |
| Single Maximum Unknown impurity | Note more than 0.2% | ND | BQL | BQL | BQL | BQL |
| Total Impurities | Note more than 1.0% | 0.08% | 0.07% | 0.08% | 0.08% | 0.08% |

Although embodiments herein have been described in considerable detail with reference to certain preferred embodiments thereof, other versions are possible. Therefore, the spirit and scope of the appended claims should not be limited to the description and the preferred versions contained within this specification.

The invention claimed is:

1. A pharmaceutical composition in the form of a liquid oral solution, consisting of:
   amitriptyline hydrochloride in an amount of 40 mg/mL based on amitriptyline;
   glycerol in an amount of from about 300 mg/mL to about 600 mg/mL;
   polysorbate 80 in an amount of about 1 mg/mL;
   one or more pharmaceutically acceptable excipients selected from a buffering agent, a chelating agent, a flavoring agent, and a sweetener; and
   water.

2. The pharmaceutical composition claim 1, wherein the glycerol is present in an amount of from about 350 mg/mL to about 450 mg/mL.

3. The pharmaceutical composition of claim 1, wherein the glycerol is present in an amount of about 380 mg/mL.

4. The pharmaceutical composition of claim 1 has a pH of from about 3.5 to about 5.5.

5. The pharmaceutical composition of claim 1 has a pH of from about 4.5.

6. The pharmaceutical composition of claim 1, wherein the pharmaceutical composition excludes ethanol.

7. A method for treating depression in a patient in need thereof, said method comprising administering a therapeutically effect amount of the pharmaceutical composition of claim 1 to the patient.

* * * * *

UNITED STATES PATENT AND TRADEMARK OFFICE
CERTIFICATE OF CORRECTION

| | |
|---|---|
| PATENT NO. | : 12,251,361 B2 |
| APPLICATION NO. | : 18/310575 |
| DATED | : March 18, 2025 |
| INVENTOR(S) | : Vijay Patel et al. |

It is certified that error appears in the above-identified patent and that said Letters Patent is hereby corrected as shown below:

In the Specification

Column 14, Line 43: "Note more than" should read -- "Not more than" --

Column 14, Line 47: "Note more than" should read -- "Not more than" --

In the Claims

Column 15, Lines 8-9 - Claim 5: "has a pH of from about 4.5." should read -- "has a pH of about 4.5." --

Signed and Sealed this
Twelfth Day of August, 2025

Coke Morgan Stewart
*Acting Director of the United States Patent and Trademark Office*